United States Patent

Penzimer et al.

(10) Patent No.: US 9,452,026 B2
(45) Date of Patent: Sep. 27, 2016

(54) APPARATUS AND METHOD FOR MEASURING A LENGTH BETWEEN IMPLANTED BONE ANCHORS

(71) Applicant: EBI, LLC, Parsippany, NJ (US)

(72) Inventors: Ray Penzimer, Morristown, NJ (US); Anthony C. DeFalco, Andover, NJ (US)

(73) Assignee: EBI, LLC, Parsippany, NJ (US)

( * ) Notice: Subject to any disclaimer, the term of this patent is extended or adjusted under 35 U.S.C. 154(b) by 372 days.

(21) Appl. No.: 14/053,694

(22) Filed: Oct. 15, 2013

(65) Prior Publication Data

US 2014/0343561 A1    Nov. 20, 2014

Related U.S. Application Data

(60) Provisional application No. 61/823,577, filed on May 15, 2013.

(51) Int. Cl.
  *A61B 17/56* (2006.01)
  *A61B 17/70* (2006.01)
  *A61B 17/60* (2006.01)
  *A61B 17/66* (2006.01)
  *A61B 17/02* (2006.01)
  *A61B 17/68* (2006.01)

(52) U.S. Cl.
  CPC .............. *A61B 90/06* (2016.02); *A61B 17/60* (2013.01); *A61B 17/66* (2013.01); *A61B 17/70* (2013.01); *A61B 17/7074* (2013.01); *A61B 2017/0256* (2013.01); *A61B 2017/681* (2013.01); *A61B 2090/061* (2016.02); *A61B 2090/067* (2016.02)

(58) Field of Classification Search
  CPC .......... A61B 2017/0256; A61B 17/60; A61B 17/66; A61B 2017/681; A61B 17/70; A61B 17/7074; A61B 19/46; A61B 2019/461; A61B 2019/467; A61B 90/06; A61B 2090/061; A61B 2090/067
  See application file for complete search history.

(56) References Cited

U.S. PATENT DOCUMENTS

| 4,957,495 A | 9/1990 | Kluger et al. |
| D560,128 S | 1/2008 | Diederich et al. |
| 7,416,553 B2 | 8/2008 | Patel et al. |
| 7,927,337 B2 | 4/2011 | Keller |
| 7,981,115 B2 | 7/2011 | Justis et al. |
| 8,881,417 B2 * | 11/2014 | Sano ............... A61B 5/107 33/512 |
| 8,906,034 B2 * | 12/2014 | Gleeson ............. A61B 17/708 606/86 A |
| 2005/0203532 A1 | 9/2005 | Ferguson et al. |
| 2008/0147078 A1 | 6/2008 | Francis et al. |
| 2009/0024134 A1 * | 1/2009 | Triplett ............. A61B 17/1757 606/102 |
| 2012/0035611 A1 | 2/2012 | Kave |
| 2012/0265212 A1 | 10/2012 | Seck |
| 2014/0107659 A1 * | 4/2014 | Walters ............. A61B 17/7074 606/102 |

FOREIGN PATENT DOCUMENTS

EP    2668908 A2 *  12/2013  ......... A61B 17/3403

* cited by examiner

*Primary Examiner* — Larry E Waggle, Jr.

(74) *Attorney, Agent, or Firm* — Schwegman Lundberg & Woessner, P.A.

(57) ABSTRACT

An apparatus for measuring a distance between first and second implanted bone anchors includes a caliper body and first and second caliper arms. The caliper body has a first longitudinal axis. The first caliper arm is slidably coupled to the caliper body and has a second longitudinal axis. The second caliper arm is rotatably coupled to the caliper body and has a third longitudinal axis. The first, second and third longitudinal axes define a plane. The second caliper arm is rotatable within the plane between a first position and a second position.

20 Claims, 7 Drawing Sheets

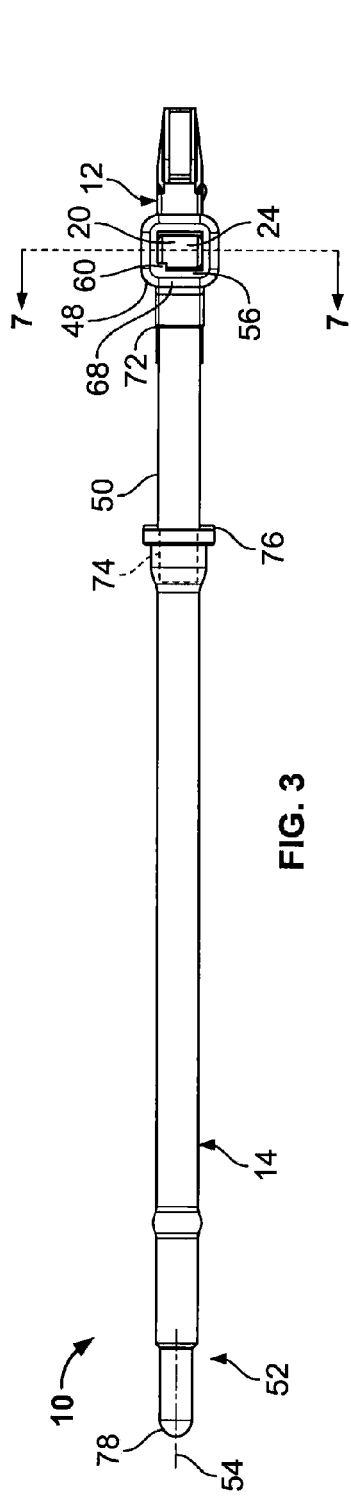
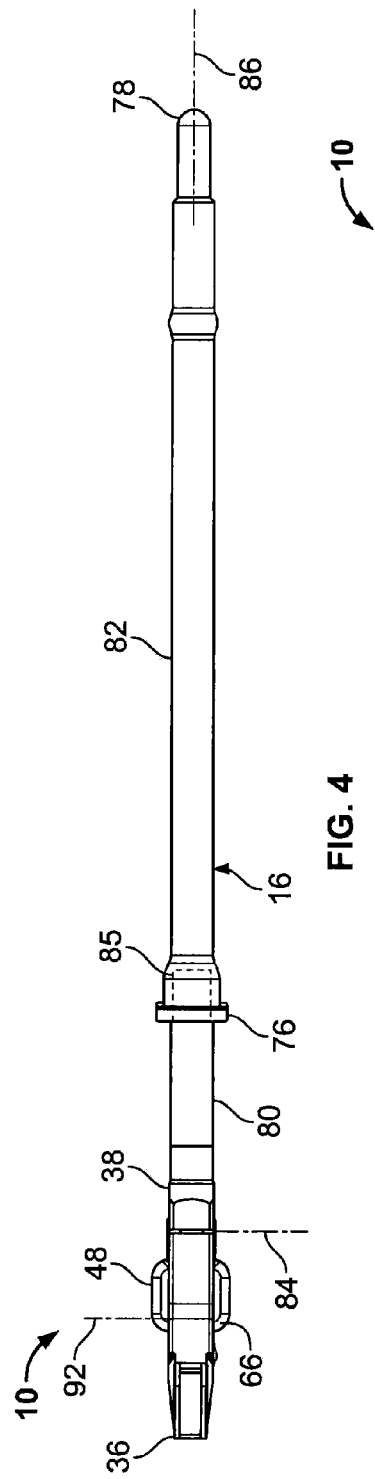
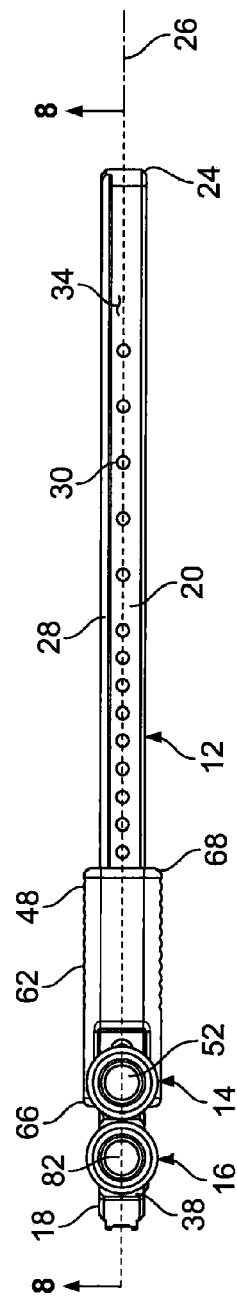
FIG. 3
FIG. 4
FIG. 5

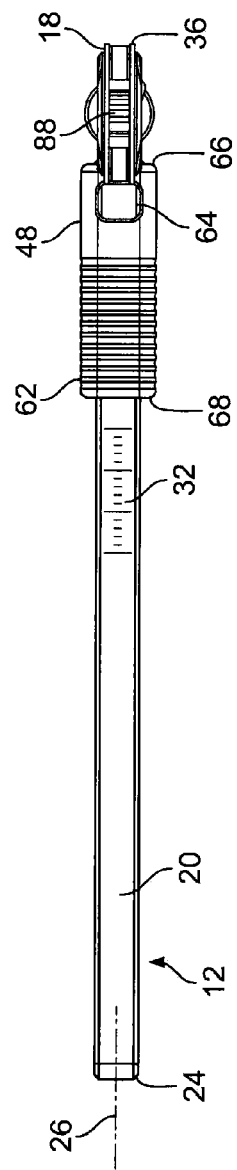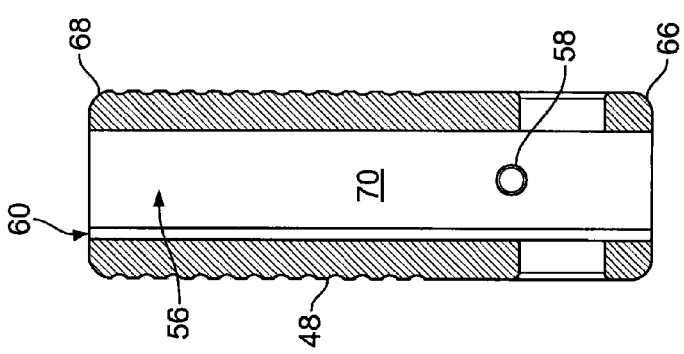

ations. The present teachings can provide an apparatus for use in a medical procedure, such as a spinal fixation procedure, which can measure the distance between one or more implants or bone anchors, including implants or bone anchors whose axes are not parallel, and thus can be used to determine the appropriate length of the interconnecting rod or anchor.

APPARATUS AND METHOD FOR MEASURING A LENGTH BETWEEN IMPLANTED BONE ANCHORS

CROSS-REFERENCE TO RELATED APPLICATIONS

This application claims the benefit of U.S. Provisional Application No. 61/823,577, filed on May 15, 2013. The entire disclosure of the above application is incorporated herein by reference.

FIELD

The present disclosure generally relates to an apparatus and method for measuring a distance between implanted bone anchors. More particularly, the present disclosure relates to an apparatus and method for measuring a distance between implanted bone anchors to establish a length of a percutaneous rod before the rod is placed in-situ for coupling the bone anchors.

BACKGROUND

This section provides background information related to the present disclosure which is not necessarily prior art.

In general, the human musculoskeletal system is composed of a variety of tissues including bone, ligaments, cartilage, muscle, and tendons. Tissue damage or deformity stemming from trauma, pathological degeneration, or congenital conditions often necessitates surgical intervention to restore function. Surgical intervention can include any surgical procedure that can restore function to the damaged tissue, which can require the use of one or more orthopedic prosthesis, such as orthopedic nails, screws, implants, etc., to restore function to the damaged tissue.

Generally, in order to stabilize various boney tissue relative to one another, such as vertebrae of the spine, one or more implants can be coupled to each of the vertebrae and interconnected via a suitable device. In one example, implants or anchors can be coupled to each of the vertebrae, and a connecting device, such as a rod, can be coupled to each of the anchors to stabilize or fix the vertebrae relative to each other. When rods and anchors are employed in a medical procedure to interconnect one or more implants, it may be desirable to provide a device suitable for in-situ measuring a distance between the implants or anchors, and thus determining the appropriate length of the interconnecting rod or anchor. Additionally, it may be desirable to provide a device suitable for measuring the distance between the implants or anchors when the longitudinal axes of the implants or anchors are not parallel.

While known devices may have proven suitable for their intended purposes, a continuous need for improvement remains in the relevant art.

SUMMARY

This section provides a general summary of the disclosure, and is not a comprehensive disclosure of its full scope or all of its features.

The present teachings can provide an apparatus for use in a medical procedure, such as a spinal fixation procedure, which can measure the distance between one or more implants or bone anchors, including implants or bone anchors whose axes are not parallel, and thus can be used to determine the appropriate length of the interconnecting rod or anchor.

According to one particular aspect, the present disclosure provides an apparatus for measuring a distance between first and second implanted bone anchors. The apparatus includes a caliper body and first and second caliper arms. The caliper body has a first longitudinal axis. The first caliper arm is slidably coupled to the caliper body and has a second longitudinal axis. The second caliper arm is rotatably coupled to the caliper body and has a third longitudinal axis. The first, second and third longitudinal axes define a plane. The second caliper arm is rotatable between a first position in the plane and a second position in the plane.

According to another particular aspect, the present disclosure provides an apparatus for measuring a distance between first and second implanted bone anchors. The apparatus includes a caliper body and first and second caliper arms. The caliper body has a first longitudinal axis. The first caliper arm is slidably coupled to the caliper body and has a second longitudinal axis. The second caliper arm is rotatably coupled to the caliper body and is rotatable about an axis perpendicular to a plane defined by the first longitudinal axis and the second longitudinal axis.

According to yet another particular aspect, the present disclosure provides a method for measuring a distance between first and second implanted bone anchors with a caliper. The caliper including a caliper body, a first caliper arm and a second caliper arm. The method includes linearly translating the first caliper arm along the caliper body. The method additionally includes generally aligning a longitudinal axis of the first caliper arm with a longitudinal axis of the first bone anchor; and generally aligning a longitudinal axis of the second caliper arm with a longitudinal axis of the second bone anchor by rotating the second caliper arm relative to the caliper body. The method further includes measuring a distance between distal ends of the first and second caliper arms as a function of linear translation of the first caliper arm along the caliper body and rotation of the second caliper arm relative to the caliper body.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 3 is a bottom view of the apparatus of FIG. 1;

FIG. 4 is a top view of the apparatus of FIG. 1;

FIG. 5 is an end view of the apparatus of FIG. 1, showing a first end of the apparatus;

FIG. 6 is an end view of the apparatus of FIG. 1, showing a second end of the apparatus;

FIG. 7 is a cross-sectional view of a slide element of the apparatus of FIG. 1, taken through line 7-7 of FIG. 3.

Corresponding reference numerals indicate corresponding parts throughout the several views of the drawings.

DETAILED DESCRIPTION

Figure 1:
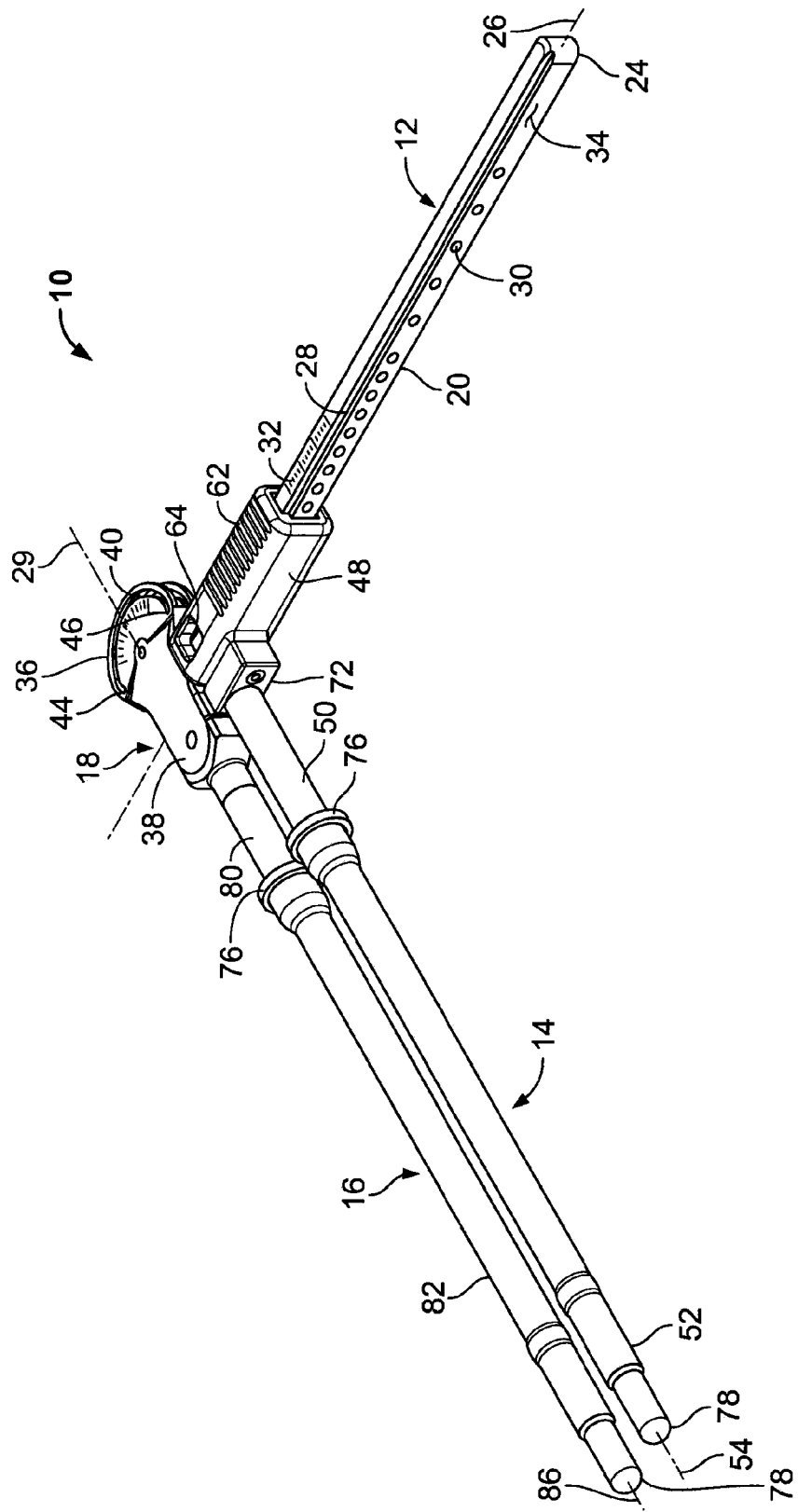
FIG. 1 is a perspective view of an apparatus for measuring a distance between implanted bone anchors in accordance with the present disclosure.

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

With reference to the Figures, an apparatus for measuring a distance between implanted bone anchors is shown, and generally identified at reference character 10. The apparatus 10 may be a caliper, and may include a caliper body 12, a first caliper arm 14, a second caliper arm 16, and a metering arm 17. The first caliper arm 14 may be slidably coupled to the caliper body 12. The second caliper arm 16 may be rotatably interconnected to the caliper body 12.

The caliper body 12 may include a head portion 18 and a rod portion 20. The rod portion 20 may have a first end 22 and a second end 24. In an example embodiment, the head portion 18 may be carried at the first end 22 of the rod portion 20. In an example embodiment, the head portion 18 may be integrally formed with the rod portion 20. In this regard, the head portion 18 and the rod portion 20 may be unitarily formed of a common material. In another embodiment, the rod portion 20 may be screwed, welded, press-fit, or otherwise suitably fastened to the head portion 18. A longitudinal axis 26 of the rod portion 20 may be substantially perpendicular to a longitudinal axis 29 of the head portion 18. The rod portion 20 may have a non-circular cross section. In the embodiment illustrated, the rod portion 20 may have a generally square cross section extending along the longitudinal axis 26 between the first end 22 and the second end 24. It will also be appreciated that the rod portion 20 may have any other suitably-shaped cross section, including a circle, rectangle or oval.

The rod portion 20 may include a groove 28, a plurality of dimples 30, and at least one first metering portion 32. The groove 28 may be formed substantially parallel to the longitudinal axis 26 of the rod portion 20, and may extend from the first end 22 to the second end 24. The dimples 30 may be formed in an outer surface 34 of the rod portion 20 between the first end 22 and the second end 24. In an example embodiment, the dimples 30 may be equally sized and evenly spaced between the first end 22 of the rod portion 20 and the second end 24 of the rod portion 20. It is also understood that the size of the dimples 30, and the spacing therebetween, may vary between the first end 22 of the rod portion 20 and the second end 24 of the rod portion 20. As will be discussed below in more detail, the groove 28 and the dimples 30 may cooperate with the first caliper arm 14 to allow the first caliper arm 14 to slide along the caliper body 12 in a direction substantially parallel to the longitudinal axis 26.

The first metering portion 32 may extend substantially parallel to the longitudinal axis 26 of the rod portion 20, from the first end 22 to the second end 24. The first metering portion 32 may include a first graduated scale show distances, such as inches, millimeters, centimeters, etc. In one configuration, the rod portion 20 includes three (3) first metering portions 32.

The head portion 18 may include a first end 36 and a second end 38. An arcuate slot 40 may be formed in the head portion 18, adjacent to the first end 36. The first end 36 may also include a second metering portion 42 extending from a first end 44 of the arcuate slot 40 to a second end 46 of the arcuate slot 40. The second metering portion 42 may include a second graduated scale showing distances, such as inches, millimeters, centimeters, etc.

Figure 8:
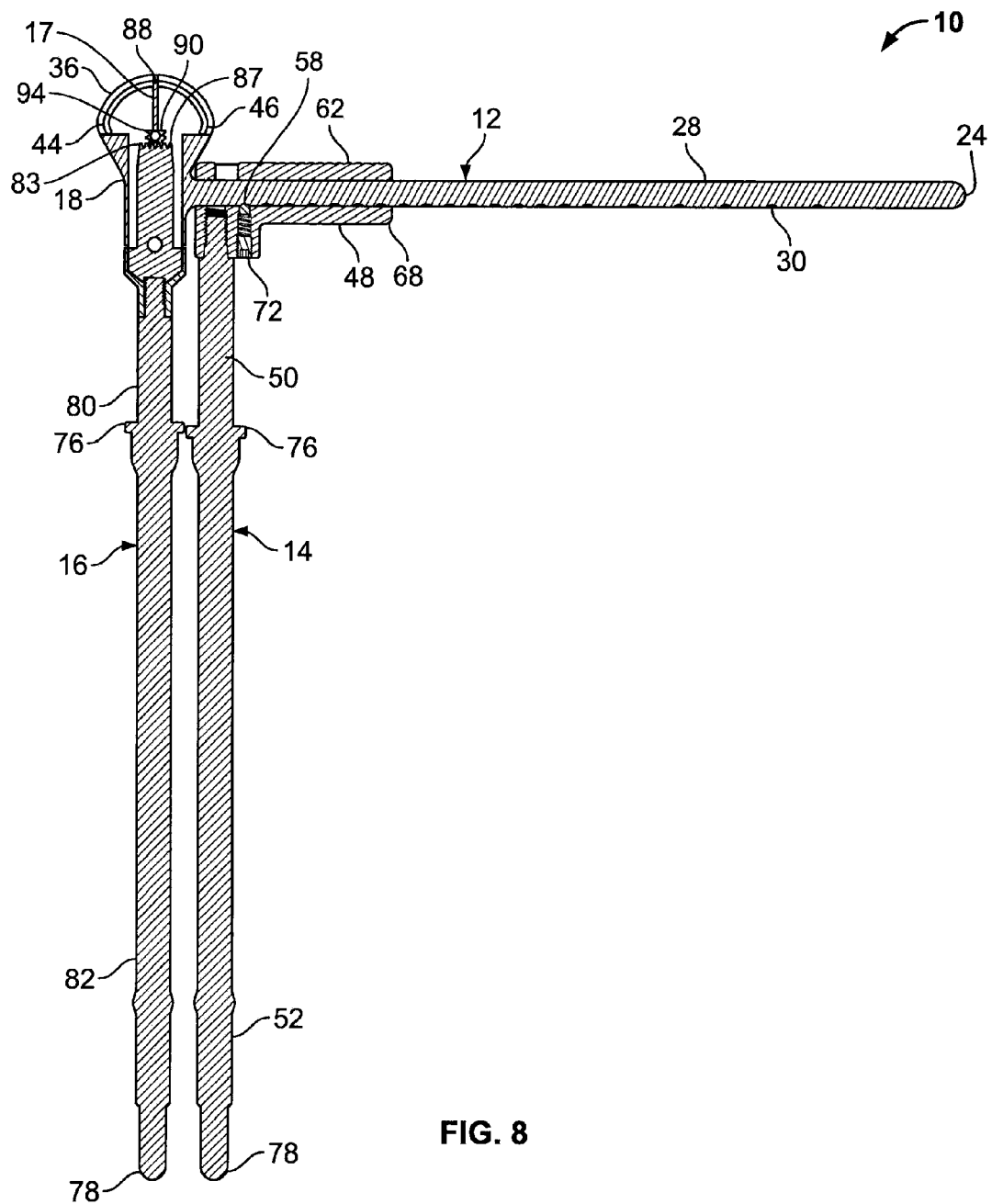
FIG. 8 is a cross-sectional view of the apparatus of FIG. 1, taken through line 8-8 of FIG. 5.

The first caliper arm 14 may include a slide element 48, a first support element 50, and a first tip element 52. A longitudinal axis 54 of the first caliper arm 14 may be substantially perpendicular to the longitudinal axis 26 of the rod portion 20. With particular reference to FIGS. 7 and 8, the slide element 48 may include a central bore 56, a nub 58, a flange 60, a plurality of rib elements 62 and an aperture 64.

The central bore 56 may extend from a first end 66 of the slide element 48 to a second end 68 of the slide element 48. The central bore 56 may be sized and shaped to closely correspond to the size and shape of the rod portion 20, such that the central bore 56 is able to slide on the rod portion 20 in a direction substantially parallel to the longitudinal axis 26 of the rod portion 20.

The flange 60 may extend from a peripheral surface 70 of the central bore 56 and slidingly engage the groove 28 of the rod portion 20. The flange 60 may prevent the slide element 48 from rotating on the rod portion 20 about the longitudinal axis 26 thereof.

The nub 58 may extend from the peripheral surface 70 of the central bore 56 to engage the plurality of dimples 30 as the slide element 48 is slid along the rod portion 20. The nub 58 may cooperate with one of the plurality of dimples 30 to positively locate the first caliper arm 14 relative to the rod portion 20 of the caliper body 12, and to prevent the slide element 48 from sliding on the rod portion 20 in the direction of the longitudinal axis 26 until a user applies a force on the slide element 48. In one configuration, the nub 58 is a set screw extending through the peripheral surface 70 of the central bore 56 by a distance that is adjustable by a user rotating the set screw. It will also be appreciated that the nub 58 may be an integral portion of the peripheral surface 70 of the central bore 56.

Figure 2A:
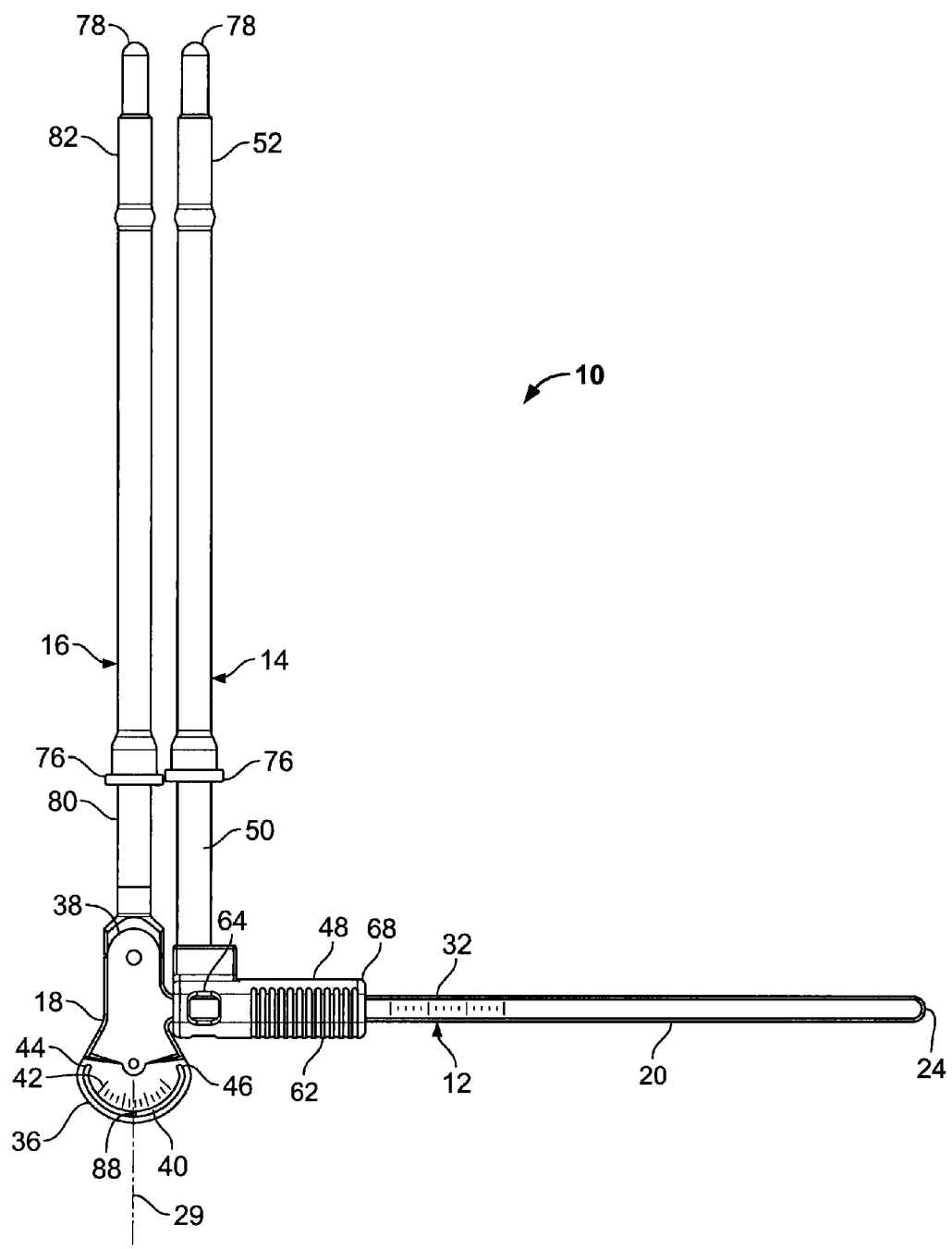
FIG. 2A is a side view of the apparatus of FIG. 1, the apparatus shown in a first configuration.
Figure 2B:
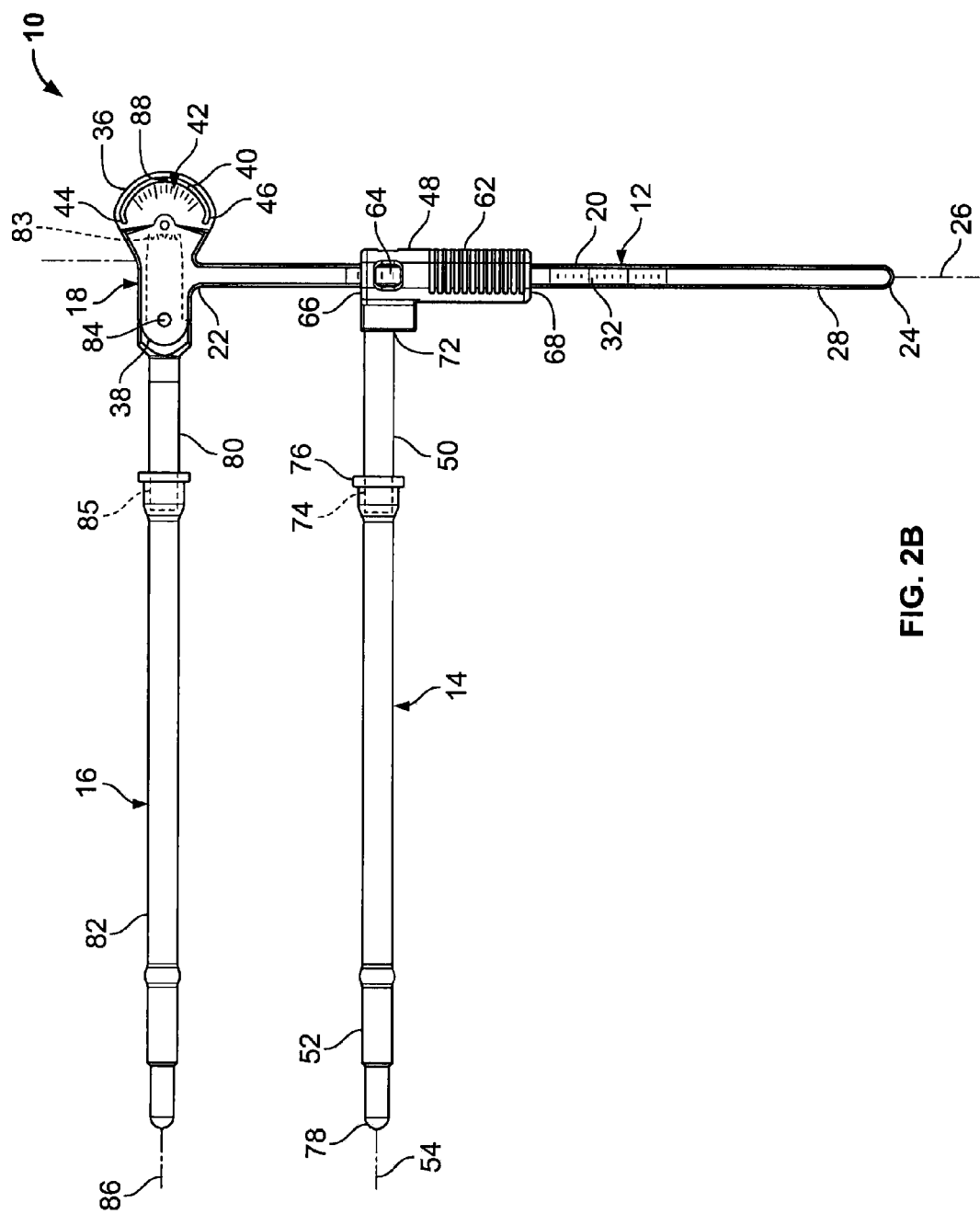
FIG. 2B is another side view of the apparatus of FIG. 1, the apparatus shown in a second configuration in which a first caliper arm is displaced relative to a caliper body.
Figure 2C:
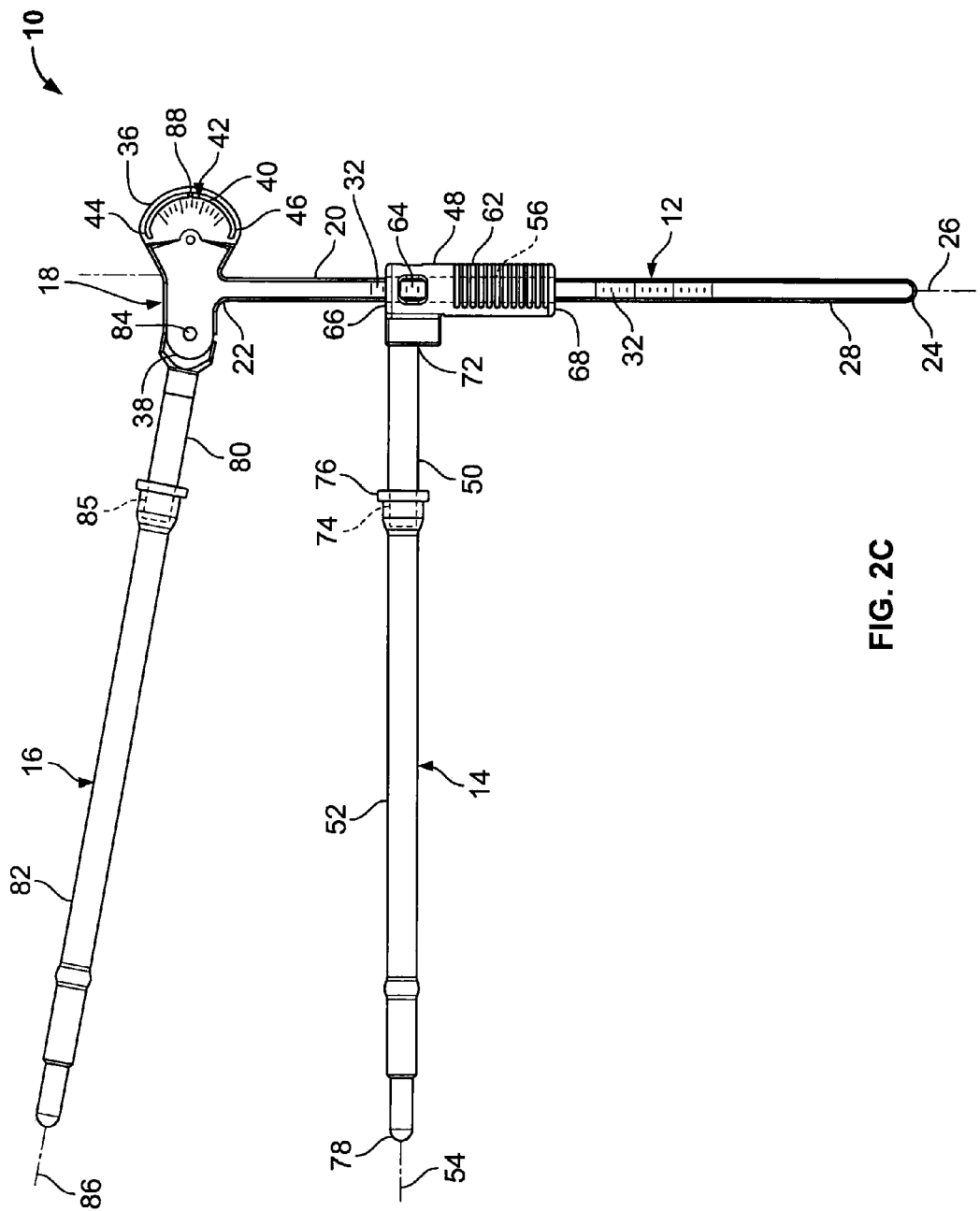
FIG. 2C is another side view of the apparatus of FIG. 1, the apparatus shown in a third configuration in which the first caliper arm is displaced relative to the caliper body and a second caliper arm is rotated relative to the caliper body.

The plurality of rib elements 62 may extend substantially around the periphery of the slide element 48 to assist a user in sliding the first caliper arm 14 along the caliper body 12. With particular reference to FIGS. 2a and 2b, the aperture 64 may extend through the wall of the slide element 48 such that the rod portion 20 (and specifically the first metering portion 32) is visible through the aperture 64 when the slide element 48 is coupled to the rod portion 20.

The first support element 50 may have a substantially cylindrical shape and include a first end 72 and a second end 74. In one embodiment, the first support element 50 is integrally formed with the slide element 48. In another embodiment, the first end 72 of the first support element 50 may be removably attached to the slide element 48 by screwing, press-fitting, or other similar attachment means, such that the first support element 50 may be a replaceable and/or disposable portion of the caliper.

The first tip element 52 may have a substantially cylindrical shape and include a first end 76 and a second end 78. In one embodiment, the first tip element 52 is integrally formed with the first support element 50. In another embodiment, the first end 76 of the first tip element 52 may be removably attached to the second end 74 of the first support element 50 by screwing, press-fitting, or other similar attachment means, such that the first tip element 52 may be a replaceable and/or disposable portion of the caliper.

The second caliper arm 16 may include a second support element 80 and a second tip element 82. The second support arm may include a first end 83 and a second end 85. The second support element 80 may be rotatably coupled to the head portion 18 between the first end 36 and the second end 38 thereof, for relative rotation about an axis 84. In one embodiment, the second support element 80 may be removably attached to the head portion 18, such that the second support element 80 may be a replaceable and/or disposable portion of the caliper. The axis 84 of the second support element 80 may be substantially perpendicular to the longitudinal axes 26, 54 of the rod portion 20 and first caliper arm 14, respectively, and perpendicular to a longitudinal axis 86 of the second caliper arm 14. More specifically, the axis 84 of the second support element 80 may be perpendicular to a plane formed by the caliper body 12 and the first support element 50, such that the second caliper arm 16 is rotatable within the plane. The first end 83 of the second support element 80 may include a series of gear teeth 87.

The second tip element 82 may be substantially the same as the first tip element 52. Accordingly, like features are described with like reference numerals in the drawings. The second tip element 82 may be integrally formed with, or removably attached to, the second end 85 of the second support element 80.

The metering arm 17 may include a first end 88 and a second end 90. The metering arm 17 may be rotatably coupled to the head portion 18, for relative rotation about a rotational axis 92. The axis 92 may be substantially parallel to the axis 84. The first end 88 of the metering arm 17 may be visible through the arcuate slot 40 formed in the head portion 18. The second end 90 of the metering arm 17 may include a series of gear teeth 94. The gear teeth 94 may be engaged with the gear teeth 87 of the second support element 80.

Operation of the apparatus 10 to measure a distance between two implants, bone anchors, or other points of measurement, will now be described in more detail. To operate the apparatus 10, the user may position the second end 78 of either the first tip element 52 or the second tip element 82 at the location of the implanted first bone anchor (not shown). The second end 78 of the first or second tip element 52, 82 may be positioned in the first bone anchor such that the longitudinal axis 54 of the first caliper arm 14 is substantially aligned with a longitudinal axis of the first bone anchor. The user may linearly translate, or slide, the first caliper arm 14 along the rod portion 20 of the caliper body 12 such that the second end 78 of the other of the first tip element 52 or the second tip element 82 is in a desired location with respect to the implanted second bone anchor (not shown). The user may rotate the second caliper arm 16 relative to the caliper body 12 such that the longitudinal axis 86 of the second caliper arm 16 is substantially aligned with a longitudinal axis of the second bone anchor.

The user may note a first measurement on the first metering portion 32. The first measurement may correspond to the location of the slide element 48 relative to the rod portion 20. The user may also note a second measurement on the second metering portion 42. The second measurement may correspond to a location of the first end 83 of the second support element 80 within the arcuate slot 40. Specifically, with respect to the second measurement, an angle of rotation of the second caliper arm 16 relative to the caliper body 12 about the axis 84 may correspond to a linear distance reflected on the second graduated scale of the second metering portion 42. The linear distance reflected on the second graduated scale may correspond to a distance necessary to angularly align the longitudinal axis of the second bone anchor with the longitudinal axis of the first bone anchor. Accordingly, the first measurement and the second measurement may be added together to calculate the total distance between the second ends 78 of the first and second tip elements 52, 82, and thus the distance between the first and second bone anchors.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An apparatus for measuring a distance between first and second implanted bone anchors, the apparatus comprising:
    a caliper body having a first longitudinal axis;
    a first caliper arm slidably coupled to the caliper body and having a second longitudinal axis, wherein the first caliper arm is disposed in a fixed angular relationship to the caliper body such that the second longitudinal axis of the first caliper arm is always substantially perpendicular to the first longitudinal axis of the caliper body; and
    a second caliper arm rotatably coupled to the caliper body and having a third longitudinal axis, wherein the first longitudinal axis, the second longitudinal axis, and the third longitudinal axis define a plane, and the second caliper arm is rotatable within the plane between a first position and a second position.

2. The apparatus of claim 1, wherein the second caliper arm is rotatable relative to the caliper body between a first configuration and a second configuration.

3. The apparatus of claim 2, wherein the third longitudinal axis of the second caliper arm and the first longitudinal axis of the caliper body define an acute angle in the first configuration and an obtuse angle in the second configuration.

4. The apparatus of claim 1, wherein the caliper body includes a first metering portion and a second metering portion, the first caliper arm operable to display a position of the first caliper arm relative to the caliper body, and the second metering portion operable to display a position of the second caliper arm relative to the caliper body.

5. The apparatus of claim 1, wherein the caliper body comprises an elongate rod portion having a cross-section including a longitudinal groove, the longitudinal groove being parallel to the first longitudinal axis and located at a corner of the rectilinear cross-section.

6. The apparatus of claim 5, wherein the first caliper arm includes a rectilinear central bore having a flange portion, the rectilinear central bore being slidably disposed on the elongate rod portion such that the flange portion is slidably disposed in the longitudinal groove.

7. The apparatus of claim 1, wherein the caliper body includes a plurality of dimples extending between a first end of the caliper body and a second end of the caliper body.

8. The apparatus of claim 7, wherein the first caliper arm includes a nub operable to engage at least one of the plurality of dimples to positively locate the first caliper arm relative to the caliper body.

9. The apparatus of claim 1, wherein:
the second caliper arm includes a second support member rotatably coupled to the caliper body, and a second tip member removably coupled to the second support member, and
the first caliper arm includes a slide element slidably coupled to the caliper body, a first support member coupled to the slide element, and a first tip member removably coupled to the first support member.

10. The apparatus of claim 9, wherein at least one of the first tip member and the second tip member are disposable.

11. The apparatus of claim 9, further comprising:
gear teeth disposed at an end of the second support member within the caliper body; and
a metering arm having a free end providing an indicator and a second end having gear teeth engaged with the gear teeth of the second support member.

12. The apparatus of claim 1, wherein the caliper body includes a head element having a first end and a second end, and the second caliper arm includes a first end and a second end, and wherein the second caliper arm is rotatably coupled to the first end of the head element between the first end and the second end of the second caliper arm.

13. The apparatus of claim 12, wherein the second end of the second caliper arm is adjacent the second end of the head element.

14. The apparatus of claim 12, wherein the second end of the head element includes an arcuate slot having a first end and a second end, and wherein the second end of the second caliper arm is adjacent the first end of the arcuate slot in a first configuration, and adjacent the second end of the arcuate slot in a second configuration.

15. The apparatus of claim 1, wherein the second caliper arm is attached to the caliper body at a rotation axis that is located in a fixed position relative to an elongate rod portion of the caliper body.

16. An apparatus for measuring a distance between first and second implanted bone anchors, the apparatus comprising:
a caliper body having a first longitudinal axis;
a first caliper arm having a slide element slidably coupled to the caliper body and having a second longitudinal axis, wherein the first caliper arm is rotationally fixed relative to the slide element; and
a second caliper arm rotatably coupled to the caliper body, the second caliper arm rotatable about an axis perpendicular to a plane defined by the first longitudinal axis and the second longitudinal axis.

17. The apparatus of claim 16, wherein the first caliper arm is substantially perpendicular to the caliper body, and wherein the second caliper arm and the caliper body define an acute angle in a first configuration and an obtuse angle in a second configuration.

18. The apparatus of claim 16, wherein the caliper body includes a first metering portion and a second metering portion, the first caliper arm operable to display a position of the first caliper arm relative to the caliper body, and the second metering portion operable to display a position of the second caliper arm relative to the caliper body.

19. A method for measuring a distance between first and second implanted bone anchors with a caliper including a caliper body, a first caliper arm and a second caliper arm configured to operate in a single plane defined by the caliper body, first caliper arm and second caliper arm, the method comprising:
linearly translating the first caliper arm along the caliper body;
generally aligning a longitudinal axis of the first caliper arm with a longitudinal axis of the first bone anchor;
generally aligning a longitudinal axis of the second caliper arm with a longitudinal axis of the second bone anchor by rotating the second caliper arm relative to the caliper body; and
measuring a distance between distal ends of the first and second caliper arms as a function of linear translation of the first caliper arm along the caliper body by viewing a first graduated scale through an aperture in the caliper body in the single plane, and rotation of the second caliper arm relative to the caliper body by viewing a second graduated scale through a slot in the caliper body in the single plane.

20. The method of claim 19, further comprising removing a first portion of the first caliper arm from the caliper and removing a second portion of the second caliper arm from the caliper.

* * * * *

UNITED STATES PATENT AND TRADEMARK OFFICE
CERTIFICATE OF CORRECTION

PATENT NO. : 9,452,026 B2  
APPLICATION NO. : 14/053694  
DATED : September 27, 2016  
INVENTOR(S) : Penzimer et al.

Page 1 of 1

It is certified that error appears in the above-identified patent and that said Letters Patent is hereby corrected as shown below:

In Column 6, Line 64, in Claim 5, after "having a", insert --rectilinear--, therefor Signed and Sealed this  
Third Day of July, 2018

Andrei Iancu  
*Director of the United States Patent and Trademark Office*